(12) United States Patent
Davey

(10) Patent No.: US 10,238,608 B2
(45) Date of Patent: Mar. 26, 2019

(54) DRUG DELIVERY PRODUCT FOR CONTROLLED DRUG DELIVERY

(71) Applicant: Neil S. Davey, Gaithersburg, MD (US)

(72) Inventor: Neil S. Davey, Gaithersburg, MD (US)

(73) Assignee: Neil S. Davey, Gaithersburg, MD (US)

( * ) Notice: Subject to any disclaimer, the term of this patent is extended or adjusted under 35 U.S.C. 154(b) by 139 days.

(21) Appl. No.: 15/370,510

(22) Filed: Dec. 6, 2016

(65) Prior Publication Data

US 2017/0079929 A1 Mar. 23, 2017

Related U.S. Application Data

(62) Division of application No. 15/011,181, filed on Jan. 29, 2016.

(60) Provisional application No. 62/109,391, filed on Jan. 29, 2015.

(51) Int. Cl.
| | |
|---|---|
| *A61K 9/50* | (2006.01) |
| *A61K 9/00* | (2006.01) |
| *A61K 9/12* | (2006.01) |

(52) U.S. Cl.
CPC .......... *A61K 9/5031* (2013.01); *A61K 9/0024* (2013.01); *A61K 9/501* (2013.01); *A61K 9/0009* (2013.01); *A61K 9/122* (2013.01)

(58) Field of Classification Search
CPC ................................................. A61K 9/0024
See application file for complete search history.

*Primary Examiner* — Kyle A Purdy
(74) *Attorney, Agent, or Firm* — Davé Law Group, LLC; Raj S. Davé

(57) ABSTRACT

Present invention provides fully or partially biodegradable drug delivery product for controlled delivery of drugs. In one embodiment, the present invention relates to a drug delivery product having a shell comprising a first material and a second material, wherein the second material comprises a first biodegradable material; a core comprising a drug, the core being enclosed by the shell; wherein the first material is distributed in a matrix of the first biodegradable material; wherein the first material is configured to create holes in the shell; wherein the holes allow the drug to be released to the exterior of the shell through the holes.

19 Claims, 3 Drawing Sheets

Matrix comprising biodegradable polymer with
drug entrapped in microporous core

Biodegradable reticulated foam

DRUG DELIVERY PRODUCT FOR CONTROLLED DRUG DELIVERY

RELATED APPLICATIONS

The present application is a division of U.S. application Ser. No. 15/011,181, entitled ""FULLY OR PARTIALLY BIODEGRADABLE DEVICE FOR CONTROLLED DRUG DELIVERY," filed on Jan. 29, 2016, which claims benefit from U.S. Provisional Application 62/109,391, entitled "FULLY OR PARTIALLY BIODEGRADABLE DEVICE FOR CONTROLLED DRUG DELIVERY," filed on Jan. 29, 2015; all of the above applications are incorporated herein by reference in their entirety.

The present invention is related U.S. Patent Publications: (1) US 20140056962 entitled "DRUG DELIVERY SYSTEM;" (2) US 20130115265 entitled "DRUG DELIVERY SYSTEM;" (3) US 20130078286 entitled "DRUG DELIVERY SYSTEM;" (4) US 20120058171 entitled "ZOOTECHNICAL DRUG DELIVERY DEVICE;" (5) US 20120052108 entitled "MACROCYCLIC LACTONE DRUG DELIVERY SYSTEM;" (6) US 20100203104 entitled "DELIVERY SYSTEM FOR RISPERIDONE;" (7) US 20100129425 entitled "VAGINAL DELIVERY SYSTEM FOR MIRTAZAPINE;" (8) US 20100104619 entitled "DELIVERY SYSTEM FOR A NON-STEROIDAL NON-IONIZED HYDROPHILIC DRUG;" (9) US 20090081278 entitled "Drug Delivery System;" (10) US 20080112892 entitled "X-Ray Visible Drug Delivery Device;" (11) US 20070141102 entitled "Drug delivery system based on polyethylene vinylacetate copolymers;" (12) US 20060280771 entitled "Drug delivery system;" (13) US 20130280334 entitled "Nanostructured Gels Capable of Controlled Release of Encapsulated Agents;" (14) US 20100129459 entitled "Biodegradable microsphere composition suitable for the controlled release of glucose controlling peptide and formulation thereof." All U.S. patents and U.S. patent Publications referred above and in the application are incorporated herein by reference in their entirety.

FIELD OF THE INVENTION

The present invention is related to a biodegradable device for controlled delivery of drugs. The device comprises micro/nano fluidic beads containing a drug embedded in a biodegradable polymer matrix, such as biodegradable foam, further enclosed by a skin or barrier layer that prevents entry of blood cells into the biodegradable foam while permitting entry of blood serum. The device is supplied with an applicator for drug delivery. The invention also relates to a method of administering the device to a patient in need thereof and use of the device for delivering a variety of drugs including small molecules to biologicals.

BACKGROUND OF THE INVENTION

Implantable device systems for controlled delivery of drugs have long been explored especially for chronic therapies. Treatment for chronic ailments requires multiple administration of a drug over a long period of time. Sustained delivery is highly desirable for delivery of bioactive agents particularly biologicals like peptides, antibodies and nucleic acid analogs. This kind of delivery would provide optimum therapeutic efficacy with minimum side effects and thereby improve patient compliance.

More preferably the implantable device therapeutic systems are built from bioabsorbable material. These therapeutic systems deliver the active to an in vivo patient site and can occupy that site for extended periods of time without being harmful to the host.

Various approaches for preparing bioabsorbable drug delivery systems have been reported in literature. U.S. Patent Application Publications US 2005/0043816 and US2007/0190108, U.S. Pat. No. 5,522,895 (Mikos), U.S. Pat. No. 5,514,378 (Mikos et al.), U.S. Pat. No. 5,133,755 (Brekke), U.S. Pat. No. 5,716,413 (Walter et al.), U.S. Pat. No. 5,607,474 (Athanasiou et al.), U.S. Pat. No. 6,306,424 (Vyakarnam et. al), U.S. Pat. No. 6,355,699 (Vyakarnam et. al), U.S. Pat. No. 5,677,355 (Shalaby et al.), U.S. Pat. No. 5,770,193 (Vacanti et al.), and U.S. Pat. No. 5,769,899 (Schwartz et al.). covers bioabsorbable delivery tissue substrate that serves as a scaffold or support onto which cells may attach.

The major weaknesses of these approaches relating to bioabsorbable three-dimensional porous scaffolds used for tissue regeneration are undesirable tissue response during the product's life cycle as the polymers biodegrade and the inability to degrade adequately in vivo, thus severely limiting their ability to serve as effective scaffolds.

US20140046255 relates to a methods and apparatus for a free-standing biodegradable patch suitable for intravascular application comprising a free-standing film or device having a mixture of a solid fibrinogen component and a solid thrombin component that, when exposed to an aqueous environment, undergoes polymerization to form fibrin.

Present invention has a valuable contribution in a state of art since the invention provides a delivery device that is biodegradable, withstands mechanical force by e.g. catheter, endoscope, arthoscope, or syringe during delivery to a biological site, but is capable of expansion by resiliently recovery to occupy and remain in the biological site.

SUMMARY OF THE INVENTION

Present invention provides fully or partially biodegradable device for controlled delivery of drugs.

In one embodiment, the present invention relates provides biodegradable device for controlled delivery of drugs, comprising a micro or nano fluidic beads that contains drug, wherein the beads are embedded in a biodegradable polymer matrix.

In one embodiment, the present invention relates provides biodegradable device for controlled delivery of drugs, comprising a micro or nano fluidic beads that contains drug, wherein the beads are embedded in a biodegradable polymer matrix, e.g., a biodegradable sol-gel or biodegradable thermoplastic polymer, further comprising a biodegradable foam. In one aspect, the biodegradable foam is present inside the polymer matrix. In another aspect, the biodegradable foam is at least partially coated on the polymer matrix. In yet another aspect, the biodegradable foam is completely coated on the polymer matrix.

In one embodiment, the present invention relates to biodegradable device for controlled delivery of drugs, comprising a micro or nano fluidic beads that contains drug, wherein the beads are embedded in a biodegradable polymer matrix, further comprising a biodegradable foam. The biodegradable foam and/or the skin or barrier layer has a defined pore size such that physical movement of a droplet is restrained and free flow through serum but not through blood cells.

In one aspect of this embodiment, the pore size in the barrier layer is less than about 10 micron. Preferably the pore size is less than about 5 micron.

In one embodiment, the present invention relates to biodegradable device for controlled delivery of drugs, comprising a micro or nano fluidic beads that contains drug, wherein the beads are embedded in a biodegradable polymer matrix, further comprising a biodegradable foam, wherein the device can be implanted into specific organs or underneath the skin for an effective local or systemic delivery of drug.

In one embodiment, the present invention relates to biodegradable device for controlled delivery of drugs, comprising a micro or nano fluidic beads that contains drug, wherein the beads are embedded in a biodegradable polymer matrix, further comprising a biodegradable foam, wherein the device is completely biodegradable such that it degrades in the body without a need for removal of the implant.

In one embodiment, the present invention relates to biodegradable device for controlled delivery of drugs, comprising a micro or nano fluidic beads that contains drug, wherein the beads are embedded in a biodegradable polymer matrix, further comprising a biodegradable foam, wherein the device provide sustained drug delivery for a prolonged period of tile. Preferably, the time period of ranges from about 1 week to about 5 years. More preferably, the time period of ranges from about 1 month to about 3 years.

The biodegradable device of the present invention is advantageous over transdermal patches. The transdermal drug delivery system has several limitations since skin forms a very effective barrier and thus the system is suitable for the only medications that have small enough size to penetrate the skin such as molecules having molecular weight less than 500. Further, molecule with sufficient aqueous and lipid solubility, having an octanol/water partition coefficient (log P) between 1 and 3 is required for permeate to transverse subcutaneous and underlying aqueous layers. Patches are known to have side effects like erythema, itching, local edema and allergic reaction can be caused by the drug, the adhesive, or other excipients in the patch formulation. Also "dose dumping is one of the serious implications of patch. In one embodiment, the biodegradable device of the present invention overcomes these limitations of transdermal patch.

In one embodiment, the present invention relates to a biodegradable device for controlled delivery of drugs, comprising a micro or nano fluidic beads that contains drug, wherein the beads are embedded in a biodegradable polymer matrix further comprising a biodegradable foam, wherein the matrix comprises an elongated shape, such as the shapes of cylinders, rods, tubes or elongated prismatic forms, or a folded, coiled, helical or other more compact configuration such as cubes, pyramids, tetrahedrons, cones, cylinders, trapezoids, parallelepipeds, ellipsoids, fusiforms, tubes or sleeves. A dimension of the matrix ranges from about 0.5 millimeter to about 5 centimeter. In a preferred aspect of embodiment, the matrix comprises single rod shaped implant having a length of about 4 centimeter and diameter of about 2 millimeter.

In one aspect of this embodiment, the biodegradable device is pre-loaded in a needle supplied with s disposable applicator.

In one embodiment, the present invention relates to a method of administering the biodegradable device for controlled delivery of drugs, comprising a micro or nano fluidic beads that contains drug, wherein the beads are embedded in a biodegradable polymer matrix, further comprising a biodegradable foam.

In one embodiment, the present invention relates to a biodegradable device for controlled delivery of drugs, comprising a micro or nano fluidic beads that contains drug, wherein the beads are embedded in a biodegradable polymer matrix further comprising biodegradable foam wherein the biodegradable polymer matrix comprising a biocompatible, cross-linked, biodegradable polyurethane, the matrix having a continuous-interconnected void phase. According to an aspect, the polyurethane degrades in a body of an animal to cause a loss of weight of the matrix and the resultant void phase is further ingrown and proliferated by tissues or biological tissue and in one embodiment, further ingrown and proliferated tissues can re-model to become substantially similar to the surrounding tissue in the body of an animal where it was placed.

In one embodiment, the present invention relates to a biodegradable device for controlled delivery of drugs, comprising a micro or nano fluidic beads that contains drug, wherein the beads are embedded in a biodegradable polymer matrix further comprising a biodegradable foam, wherein the device is suitable for delivery of small molecules having molecular weight less than 500 as well as large biologics entities like peptides, antibodies and nucleic acid analogs such as modified RNA, small interfering RNA, anti-sense DNA or fragments thereof.

In one embodiment, the present invention relates to a biodegradable device for controlled delivery of drugs, comprising a micro or nano fluidic beads that contains drug, wherein the beads are embedded in a biodegradable polymer matrix further comprising a biodegradable foam, wherein the device is suitable for delivery of lidocaine, diclofenec, clonidine, estradiol, estradiol/norethindrone acetate, estradiol/levonorgestrel, fentanyl, methylphenidate, nicotine, norelgestromin/ethinyl estradiol, nitroglycerin, oxybutynin, scopolamine, selegiline, testosterone, rivastigmine, rotogotine.

In one embodiment, the present invention relates to a biodegradable device for controlled delivery of drugs, comprising a micro or nano fluidic beads that contains drug, wherein the beads are embedded in a biodegradable polymer matrix further comprising a biodegradable foam, wherein the device is suitable for delivery of long-term sustained release of insulin or analogs thereof, GLP-1 or analogs thereof, alone or in combination of other therapies, to treat diabetes or other metabolic conditions.

In one aspect of this embodiment, the biodegradable device is suitable for delivery of long-term release of contraceptive hormones, combination of estrogen or progestin or singular delivery of progesterone alone and serves as contraceptive aid for women.

In one aspect of this embodiment, the biodegradable device is suitable for delivery of long-term therapeutic benefit for ocular diseases, such as age related macular degeneration, dry eye and various others.

In one aspect of this embodiment, the biodegradable device is suitable for delivery of any small molecule or biologic therapy to treat urinary bladder complications such as incontinence, yeast infections, bladder cancer and various others.

In one aspect of this embodiment, the biodegradable device is suitable for delivery of therapeutic molecules to the male reproductive organs as a means to treat medical conditions such as erectile dysfunction, premature ejaculation, testicular cancer and various others pertaining to male reproductive system.

In one aspect of this embodiment the biodegradable device is suitable for delivery of therapeutic molecules to female reproductive organs, uterus and ovaries, to treat medical conditions such as endometriosis, uterine fibroids, ovarian cancer, uterine cancer, poly cystic ovarian syndrome, and various other diseases pertaining to female reproductive system.

In one aspect of this embodiment, the biodegradable device is suitable for delivery of therapeutic molecules to heart to treat conditions such as heart failure, myocardial ischemia, and various other heart diseases.

In one aspect of this embodiment, the biodegradable device is suitable for delivery of therapeutic molecules into the adipose tissue to treat conditions such as metabolic syndrome, diabetes, hypercholesterolemia, hypertriglyceridemia and various others.

In another embodiment, the present invention relates to a biodegradable device for controlled delivery of drugs, comprising a micro or nano fluidic beads that contains drug, wherein the beads are embedded in a biodegradable polymer matrix, further comprising a biodegradable foam wherein a top coating can be applied to delay release of the active agent. In another embodiment, a top coating can be used as the matrix for the delivery of a second active agent. A layered coating, comprising respective layers of fast- and slow-hydrolyzing polymer, can be used to stage release of the active agent or to control release of different active agents placed in the different layers. Polymer blends may also be used to control the release rate of different active agents or to provide a desirable balance of coating characteristics (e.g., elasticity, toughness) and drug delivery characteristics (e.g., release profile). Polymers with differing solvent solubilities can be used to build-up different polymer layers that may be used to deliver different active agents or to control the release profile of a active agents.

The amount of an active agent present depends upon the particular the active agent employed and medical condition being treated. In one embodiment, the active agent is present in an effective amount. In another embodiment, the amount of the active agent represents from about 0.01% to about 60% of the coating by weight. In another embodiment, the amount of the active agent represents from about 0.01% to about 40% of the coating by weight. In another embodiment, the amount of the active agent represents from about 0.1% to about 20% of the coating by weight.

Another embodiment relates to a device comprising a shell comprising a first material and a second material, wherein the second material comprises a biodegradable material; a core comprising a pharmaceutically effective composition, the core being enclosed by the shell; wherein the first material is distributed in a matrix of the biodegradable material; wherein the first material is configured to create holes in the shell; wherein the holes allow the pharmaceutically effective composition to be released to the exterior of the shell through the holes. In one embodiment, the shell could be made by polymerizing a silica-functionalized monomer to form a silica-containing biodegradable polymer shell.

Preferably, the first material comprises a metal-containing material that can be heated to form the holes or a biodegradable material that degrades over time. Preferably, the metal-containing material if configured to be heated under radiation, before or after implanting or attaching the device in or on a body of a human or an animal, to form the holes. Preferably, the metal-containing material comprises metallic particles. Preferably, the metallic component comprises an iron-containing material or an iron-containing polymer. Preferably, the metallic particles comprise iron-containing particles or an iron-containing polymer. Preferably, the first material comprises a biodegradable material. Preferably, the first and second materials comprise polymers. Preferably, the first material comprises poly lactid acid (PLA) or an iron-containing polymer and the second biodegradable material comprises poly ε-caprolactone (PCL). Preferably, the core comprises an emulsion or beads of the pharmaceutically effective composition and a polymer.

Preferably, the pharmaceutically effective composition comprises a targeting material or targeting molecule that binds to a certain organ, object or a specific site within a body of a human or an animal.

DETAILED DESCRIPTION OF THE INVENTION

Figure 1:
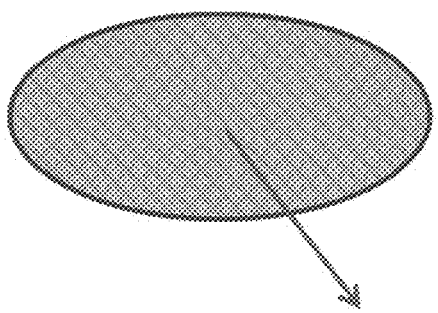
FIG. 1: Biodegradable device comprising a micro or nano fluidic beads that contains drug, wherein the beads are embedded in a biodegradable polymer matrix, further comprising a biodegradable foam.
Figure 2:
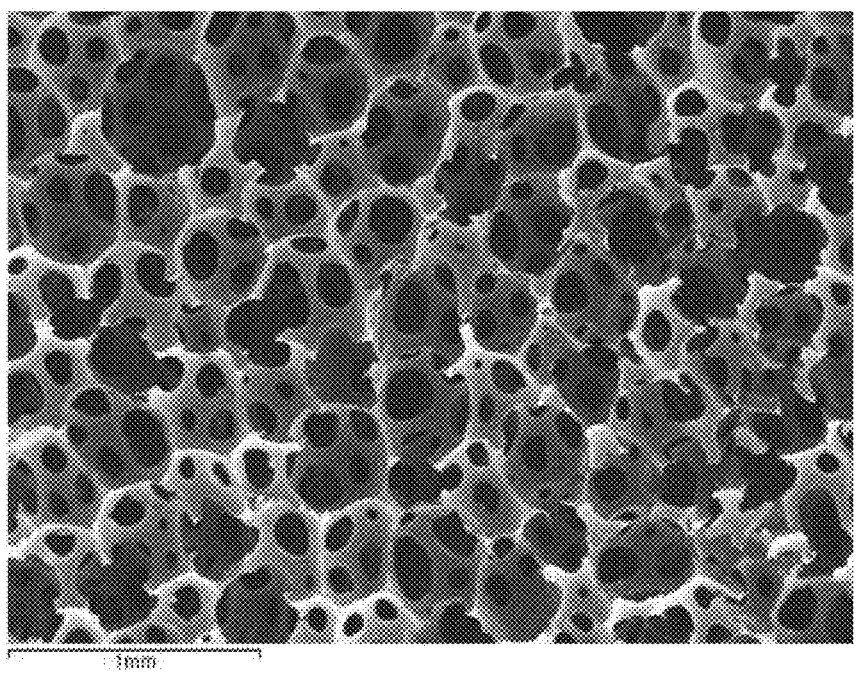
FIG. 2: Biodegradable reticulated foam formed after thermal reticulation wherein the boundary skin layer formed during the foaming process was trimmed and removed prior to subjecting the as-made foam to thermal reticulation.
Figure 3:
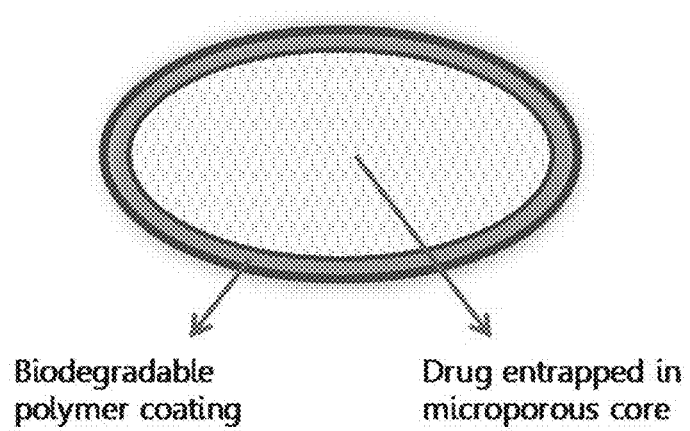
FIG. 3: Biodegradable device comprising a micro or nano fluidic beads that contains drug, wherein the beads are embedded in a biodegradable polymer matrix, further coated with a biodegradable foam.
Figure 4:
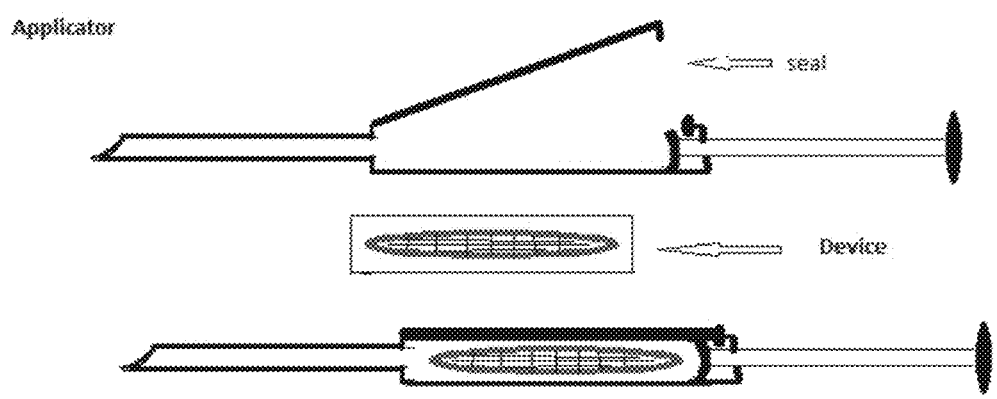
FIG. 4: Biodegradable device along with its applicator.

Present invention provides biodegradable device for controlled delivery of drugs.

"Drug" in context of the present invention may include a small molecule therapeutic active agent, a biological active agent. The terms drug, active, active agent, therapeutic agent are used interchangeably.

In one embodiment, the present invention relates provides biodegradable device for controlled delivery of drugs, comprising a micro or nano fluidic beads that contains drug, wherein the beads are embedded in a biodegradable polymer matrix.

"Micro or nano beads" or "micro or nano fluidic beads" in context of the present invention have an ability to release a drug in a controlled manner and comprises of micro droplet embedded or floating in a natural foam and surrounded by a biodegradable mesh made of natural material or a biodegradable polymer. The beads may be spherical or substantially spherical in shape, having its largest transverse dimension is equivalent to the diameter of the bead. Alternatively the bead may be non-spherical, for example, ellipsoidal or tetrahedral in shape having its largest transverse dimension is equivalent to the greatest distance within the bead from one bead surface to another e.g., the major axis length for an ellipsoidal bead or the length of the longest side for a tetrahedral bead.

The embodiments herein describes a drug delivery system a combination, comprising of a core comprising micro/nano-fluidic beads that contains the active pharmaceutical or biologic agent with an ability to release the drug in a controlled release fashion. The core could be surrounded by a biodegradable mesh or patch with a defined pore size of less than 10 micron, preferably less than 5 microns, to restrain the physical movement of the droplet but to allow the free flow of serum but not blood cells from accessing the core droplet. The core could also be surrounded by a biodegradable barrier such as a biodegradable polymer skin layer having channels of less than 5 micron width. The channels could run from one end of the core to the other end of the core, if the core is shaped like a cylinder, for example. The channels could run straight from one end of the core to the other end of the core or they could run in a spiral fashion.

The time for biodegradability of the beads ($t_1$) is shorter than the time for biodegradability of foam or polymer matrix ($t_2$) in which the beads are embedded, and in turn the time for biodegradability of the foam or polymer matrix is shorter than the time for biodegradability of the skin layer ($t_3$), such as mesh, or a barrier layer surrounding the foam or polymer matrix. Applying these time scales ($t_1 < t_2 < t_3$) for the biodegradability of the different components of the drug delivery device of the embodiments herein, even when the foam degraded it would not cause an individual to have any hypersensitive reaction from the degradation of the foam as the degraded foam products would remain enclosed within the skin or barrier layer, which would degrade the last. In one embodiment, $t_1 < t_2 < t_3$, for example, could be 1-3 months, 3-6 months and 6-12 months, respectively.

Yet in another embodiment, the core could be surrounded by a biodegradable barrier such as a biodegradable polymer skin layer comprising a biodegradable polymer that swells and creates openings through biodegradable polymer skin layer, wherein the openings are large enough to allow the drug to leach out of the core into the body of a human or animal into which the drug delivery device is implanted.

In yet another embodiment, the biodegradable foam of the core could be open cell biodegradable foam and the drug containing beads fixed to the walls of the open cell biodegradable foam. For example, the open cell biodegradable foam could have an average cell size of about 300 micron with openings between adjacent cells of about 200 micron, and the diameter of drug containing beads could be about 40 micron, with the bead wall having a thickness of 1-20 micron to allow beads to rupture at different times within the body of a human or animal into which the drug delivery device is implanted. The beads could be bonded to the walls of the open cell biodegradable foam by coating the beads with a coating layer that functions as an adhesive between the beads and the cell walls. Alternatively, the coating layer can be crosslinked so as to form a bond, such as a covalent bond, between the beads and the cell wells.

The open cell biodegradable foam could be reticulated foam formed after thermal reticulation such those disclosed in U.S. Pat. No. 8,801,801, entitled "AT LEAST PARTIALLY RESORBABLE RETICULATED ELASTOMERIC MATRIX ELEMENTS AND METHODS OF MAKING SAME," which is incorporated herein in its entirety. In the biodegradable reticulated foam, the boundary skin layer formed during the foaming process was trimmed and removed prior to subjecting the as-made foam to thermal reticulation. The open cell biodegradable foam in the embodiments herein is generally resilient to crushing when implanted within the body of a human or animal; thereby the open cell biodegradable foam substantially maintains its original shape before implantation even after implantation within the body of the human or animal.

In yet another embodiment, the biodegradable foam could be closed cell biodegradable foam formed by bonding together a plurality of drug containing beads. The diameter of drug containing beads could be about 40 micron, with the bead wall having a thickness in the range of 1-20 micron to allow beads to rupture at different times within the body of a human or animal into which the drug delivery device is implanted.

In yet another embodiment, the biodegradable device for controlled delivery of drugs comprises of three regions: (1) a core, (2) an intermediate layer and (3) an outer skin or barrier layer. The core is an inner structure within the intermediate layer. The core may or may not include the drug containing beads. In case the core contains the drug containing beads, the intermediate layer could contain an additional drug or a material that regulates the flow of the drug released from the core into the patient. In case the core does not contain the drug containing beads, the intermediate layer contains the drug containing beads; it is the compartment which contains the drug to be delivered to the patient and is covered by the skin layer. The core could comprise a biodegradable foam. The intermediate layer surrounding the core could be formed of a biodegradable polymer. The core can also contribute to the strength or flexibility of the device and to increase drug substance efficiency.

The drug delivery device of the embodiments herein can be implanted into specific organs, such as vagina, or underneath the skin for an effective local or systemic delivery of the pharmaceutical agent. In one embodiment, the present invention relates provides biodegradable device for controlled delivery of drugs, comprising a micro or nano fluidic beads that contains drug, wherein the beads are embedded in a biodegradable polymer matrix, further comprising biodegradable foam. In one aspect, the biodegradable foam is present inside the polymer matrix. In another aspect, the biodegradable foam is at least partially coated on the polymer matrix. In yet another aspect, the biodegradable foam is completely coated on the polymer matrix.

In one embodiment, the present invention relates to biodegradable device for controlled delivery of drugs, comprising a micro or nano fluidic beads that contains drug, wherein the beads are embedded in a biodegradable polymer matrix, further comprising biodegradable foam. The biodegradable foam and/or the skin or barrier layer has a defined pore size such that physical movement of a droplet is restrained and free flow through serum but not through blood cells.

In one embodiment, the present invention relates to biodegradable device for controlled delivery of drugs, comprising a micro or nano fluidic beads that contains drug, wherein the beads are embedded in a biodegradable polymer matrix, further comprising a biodegradable foam, wherein the device can be implanted into specific organs or underneath the skin for an effective local or systemic delivery of drug.

In one embodiment, the present invention relates to biodegradable device for controlled delivery of drugs, comprising a micro or nano fluidic beads that contains drug, wherein the beads are embedded in a biodegradable polymer matrix, further comprising a biodegradable foam, wherein the device is completely biodegradable such that it degrades in the body without a need for removal of the implant.

In one embodiment, the present invention relates to biodegradable device for controlled delivery of drugs, comprising a micro or nano fluidic beads that contains drug, wherein the beads are embedded in a biodegradable polymer matrix, further comprising a biodegradable foam, wherein the device provide sustained drug delivery for a prolonged period of tile. Preferably, the time period of ranges from about 1 week to about 5 years. More preferably, the time period of ranges from about 1 month to about 3 years.

The beads used in the drug delivery device of the embodiments herein can be made by microfluidics. Microfluidics-based technology enables precise control and manipulation of fluids constrained to micron-sized capillaries. Advantages of microfluidics include reduced sample size and reagent consumption, short processing times, enhanced sensitivity, real-time analysis, and automation. More specifically, drop-based microfluidics allows for the creation of micron-sized emulsions that can hold discrete picoliter volumes, with drop-making frequencies of greater than 2,000 drops per second (2 kHz).

Soft lithography techniques could be employed to fabricate microfluidic devices for bead fabrication. For example, in one embodiment, AutoCAD software was used to generate a UV photomask containing micron-sized capillaries of desired structure and dimension. A silicon wafer was coated with UV photoresist, on which the photomask was placed. After UV exposure, the silicon wafer was developed with propylene glycol monomethyl ether acetate (PGMEA) to generate a positive resist with the desired channels exposed. Polydimethylsiloxane (PDMS) was poured atop the positive resist and incubated at 65° C. overnight. After removing the PDMS (now a negative resist with the desired channels) from the silicon wafer, the inlets were punched and the PDMS was bonded to glass via plasma-activated bonding. The devices were treated with hydrophobic Aquapel to prevent the wetting of channels during drop formation. The device for droplet formation is disclosed in U.S. Patent Publication 20120222748, entitled "DROPLET CREATION TECHNIQUES," which is incorporated herein by reference in its entirety.

Additional U.S. patents and Publications related to droplet formation and are incorporated herein by reference in their entirety are:

(1) U.S. Pat. No. 7,776,927 B2—This is a patent broadly describes methods of droplet generation and describes some potential uses in drug delivery.

(2) US20120141589 A1—This patent describes some compounds (such as $CaCO_3$) with which the microfluidic emulsions could be made with depending on the drug encapsulated in the emulsion, droplets and beads.

(3) US20130202657—This publication describes a microfoam for drug delivery. Such a microfoam could be incorporated as the foam or mesh in the drug delivery device of the embodiments herein.

(4) U.S. Pat. No. 6,858,220 B2—This patent discloses an implantable biocompatible microfluidic drug delivery system using only channels, but not microbeads containing a drug.

(5) US20130035574, US20130035660—These publications describe the actual chip/patch rather than the microbeads. However, the publications use microfluidics as well as scaffolding for drug delivery.

(6) U.S. Pat. No. 7,560,036 B2—This patent describes in detail the fabrication of the surface substrate, and uses microneedles for drug delivery.

The drug containing beads could be made from droplets, for example, formed in accordance with the droplet creation techniques disclosed in U.S. Patent Publication US20120222748, for the drug delivery device of the embodiments by crosslinking biodegradable polymer of the shell of the drug containing beads. The crosslinking density of the biodegradable polymer of the shell could be varied such that even for the same shell thickness, the drug containing beads with low crosslinking density would rupture at earlier time than the drug containing beads with high crosslinking density when the drug containing beads are exposed to blood serum or any other bodily fluid, for example.

The drug containing beads in the embodiments herein can be sustained release particles having an inner core, which could be hollow or solid or porous, containing an active pharmaceutical ingredient, an optional intermediate coating substantially surrounding the inner core, and an outer coating substantially surrounding the optional intermediate coating comprising a pH independent polymer such as that disclosed in U.S. Patent Publication 20080187579, entitled "Extended-release dosage form," which is incorporated herein in its entirety. The drug delivery device of the embodiments herein could have two or more bead populations wherein each of the bead populations has a different drug release profile. The method of preparing an extended release dosage composition comprising one or more bead populations could be that disclosed in U.S. Patent Publication 20080187579, with an additional requirement that the beads are made of biodegradable material such as a biodegradable polymer.

The biodegradable device of the present invention is advantageous over transdermal patches. The transdermal drug delivery system has several limitations since skin forms a very effective barrier and thus the system is suitable for the only medications that have small enough size to penetrate the skin such as molecules having molecular weight less than 500. Further, molecule with sufficient aqueous and lipid solubility, having a octanol/water partition coefficient (log P) between 1 and 3 is required for permeate to transverse subcutaneous and underlying aqueous layers. Patches are known to have side effects like erythema, itching, local edema and allergic reaction can be caused by the drug, the adhesive, or other excipients in the patch formulation. Also "dose dumping is one of the serious implications of patch. In one embodiment, the biodegradable device of the present invention overcomes these limitations of transdermal patch.

In one embodiment, the present invention relates to a biodegradable device for controlled delivery of drugs, comprising a micro or nano fluidic beads that contains drug, wherein the beads are embedded in a biodegradable polymer matrix further comprising a biodegradable foam, wherein the matrix comprises an elongated shape, such as the shapes of cylinders, rods, tubes or elongated prismatic forms, or a folded, coiled, helical or other more compact configuration such as cubes, pyramids, tetrahedrons, cones, cylinders, trapezoids, parallelepipeds, ellipsoids, fusiforms, tubes or sleeves. A dimension of the matrix ranges from about 0.5 millimeter to about 5 centimeter. In a preferred aspect of embodiment, the matrix comprises a single rod shaped implant having a length of about 4 centimeter and diameter of about 2 millimeter.

In one aspect of this embodiment, the biodegradable device is preloaded in a needle supplied with s disposable applicator.

In one embodiment the present invention relates to a method of administering the biodegradable device for controlled delivery of drugs, comprising a micro or nano fluidic beads that contains drug, wherein the beads are embedded in a biodegradable polymer matrix, further comprising a biodegradable foam.

In one embodiment, the present invention relates to a biodegradable device for controlled delivery of drugs, comprising a micro or nano fluidic beads that contains drug, wherein the beads are embedded in a biodegradable polymer matrix further comprising a biodegradable foam wherein the biodegradable polymer matrix comprising a biocompatible, cross-linked, biodegradable material, collagen, fibronectin, elastin, hyaluronic acid or a mixture thereof.

In one embodiment the biodegradable polymer matrix material for the bead, foam and/or the skin layer or mesh surrounding the foam may include polyglycolic acid ("PGA"), polylactic acid ("PLA"), polycaprolactic acid ("PCL"), poly-p-dioxanone ("PDO"), PGA/PLA copolymers, PGA/PCL copolymers, PGA/PDO copolymers, PLA/PCL copolymers, PLA/PDO copolymers, PCL/PDO copolymers or combinations thereof.

In another embodiment, the biodegradable polymer matrix material may include polycarbonate polyurethanes, polycarbonate urea-urethanes, polyether polyurethanes, poly(carbonate-co-ether) urea-urethanes, polysiloxanes and the like.

In one embodiment, the present invention relates to a biodegradable device for controlled delivery of drugs, comprising a micro or nano fluidic beads that contains drug, wherein the beads are embedded in a biodegradable polymer matrix further comprising a biodegradable foam wherein the biodegradable polymer matrix comprising a biocompatible, cross-linked, biodegradable polyurethane, the matrix having a continuous-interconnected void phase. According to an aspect, the polyurethane degrades in a body of an animal to cause a loss of weight of the matrix and the resultant void phase is further ingrown and proliferated by tissues or biological tissue and in one embodiment, further ingrown and proliferated tissues can re-model to become substantially similar to the surrounding tissue in the body of an animal where it was placed.

In one aspect, the polyurethane matrix comprises biodegradable, polyol-derived soft segments and isocyanate-derived hard segments. According to an aspect, the matrix has substantially non-crystalline isocyanate-derived hard segments. According to an aspect, the polyurethane matrix is derived from an amount of glycerol sufficient to at least partially cross-link the isocyanate-derived hard segments. According to an aspect, the isocyanate-derived hard segments are substantially free from biuret and/or allophanate and/or isocyanurate groups.

According to an aspect, the polyurethane matrix comprises at least one at least one auxiliary agent which may comprise glycerol, water, surfactants, cell-openers, viscosity modifiers, catalysts and solvents.

Surfactant may include but are not limited to TEGOSTAB® BF 2370 from Goldschmidt, D.C. 5241 from Dow Corning (Midland, Mich.), polysorbate, poloxamer and other non-ionic organosilicones, such as the polydimethylsiloxane types available from Dow Corning, Air Products and General Electric (Waterford, N.Y.).

Catalysts may include but are not limited to tertiary amine catalysts like the TOTYCAT® line from Toyo Soda Co. (Japan), the TEXACAT® line from Texaco Chemical Co. (Austin, Tex.), the KOSMOS® and TEGO® lines from Th. Goldschmidt Co. (Germany), the DMP® line from Rohm and Haas (Philadelphia, Pa.), the KAO LIZER® line from Kao Corp. (Japan), and the QUINCAT® line from Enterprise Chemical Co. (Altamonte Springs, Fla.). Exemplary organotin catalysts include the FOMREZ® and FOMREZ UL® lines from Witco Corporation (Middlebury, Conn.), the COCURE® and COSCAT® lines from Cosan Chemical Co. (Carlstadt, N.J.), and the DABCO® and POLYCAT® lines from Air Products.

Cell-opener may include ORTEGOL® 501 from Goldschmidt.)

The viscosity modifier propylene carbonate (from Sigma-Aldrich)

Solvents include by are not limited to: acetone, N-methylpyrrolidone ("NMP"), DMSO, toluene, methylene chloride, chloroform, 1,1,2-trichloroethane ("TCE"), various freons, dioxane, ethyl acetate, THF, DMF and DMAC.

According to an aspect, the matrix comprising biocompatible, cross-linked, biodegradable polyurethane, the matrix having a continuous-interconnected void phase, wherein said matrix is configured to be in-grown by a biological tissue. The continuous-interconnected void phase is termed as reticulated matrix and is interconnected and intercommunicating networks of cells, pores, and voids to permit ingrowth and proliferation of tissue into the matrix interiors or in one embodiment into the device interiors.

In one embodiment, the present invention relates provides biodegradable device for controlled delivery of drugs, comprising a micro or nano fluidic beads that contains drug, wherein the beads are embedded in a biodegradable polymer matrix further comprising a biodegradable foam, wherein the device is suitable for delivery of small molecules having molecular weight less than 500 as well as large biologics entities like peptides, antibodies and nucleic acid analogs such as modified RNA, small interfering RNA, anti-sense DNA or fragments thereof.

In one embodiment, the present invention relates to a biodegradable device for controlled delivery of drugs, comprising a micro or nano fluidic beads that contains drug, wherein the beads are embedded in a biodegradable polymer matrix further comprising a biodegradable foam, wherein the device is suitable for delivery of lidocaine, diclofenec, clonidine, estradiol, estradiol/norethindrone acetate, estradiol/levonorgestrel, fentanyl, methylphenidate, nicotine, norelgestromin/ethinyl estradiol, nitroglycerin, oxybutynin, scopolamine, selegiline, testosterone, rivastigmine, rotogotine.

In one embodiment the present invention relates to a biodegradable device for controlled delivery of drugs, comprising a micro or nano fluidic beads that contains drug, wherein the beads are embedded in a biodegradable polymer matrix further comprising a biodegradable foam, wherein the device is suitable for delivery of long-term sustained release of insulin or analogs thereof, GLP-1 or analogs thereof, alone or in combination of other therapies, to treat diabetes or other metabolic conditions.

In one aspect of this embodiment, the biodegradable device is suitable for delivery of long-term release of contraceptive hormones, combination of estrogen or progestin or singular delivery of progesterone alone and serves as contraceptive aid for women.

In one aspect of this embodiment, the biodegradable device is suitable for delivery of long-term therapeutic benefit for ocular diseases, such as age related macular degeneration, dry eye and various others.

In one aspect of this embodiment, the biodegradable device is suitable for delivery of any small molecule or biologic therapy to treat urinary bladder complications such as incontinence, yeast infections, bladder cancer and various others.

In one aspect of this embodiment, the biodegradable device is suitable for delivery of therapeutic molecules to the male reproductive organs as a means to treat medical conditions such as erectile dysfunction, premature ejaculation, testicular cancer and various others pertaining to male reproductive system.

In one aspect of this embodiment, the biodegradable device is suitable for delivery of therapeutic molecules to female reproductive organs, uterus and ovaries, to treat medical conditions such as endometriosis, uterine fibroids, ovarian cancer, uterine cancer, poly cystic ovarian syndrome, and various other diseases pertaining to female reproductive system.

In one aspect of this embodiment, the biodegradable device is suitable for delivery of therapeutic molecules to heart to treat conditions such as heart failure, myocardial ischemia, and various other heart diseases.

In one aspect of this embodiment, the biodegradable device is suitable for delivery of therapeutic molecules into the adipose tissue to treat conditions such as metabolic syndrome, diabetes, hypercholesterolemia, hypertriglyceridemia and various others.

In another embodiment, the present invention relates to a biodegradable device for controlled delivery of drugs, comprising a micro or nano fluidic beads that contains drug, wherein the beads are embedded in a biodegradable polymer matrix, further comprising a biodegradable foam wherein a top coating can be applied to delay release of the active agent. In another embodiment, a top coating can be used as the matrix for the delivery of a second active agent. A layered coating, comprising respective layers of fast- and slow-hydrolyzing polymer, can be used to stage release of the active agent or to control release of different active agents placed in the different layers. Polymer blends may also be used to control the release rate of different active agents or to provide a desirable balance of coating characteristics (e.g., elasticity, toughness) and drug delivery characteristics (e.g., release profile). Polymers with differing solvent solubilities can be used to build-up different polymer layers that may be used to deliver different active agents or to control the release profile of active agents.

The amount of an active agent present depends upon the particular the active agent employed and medical condition being treated. In one embodiment, the active agent is present in an effective amount. In another embodiment, the amount of the active agent represents from about 0.01% to about 60% of the coating by weight. In another embodiment, the amount of the active agent represents from about 0.01% to about 40% of the coating by weight. In another embodiment, the amount of the active agent represents from about 0.1% to about 20% of the coating by weight.

The drug delivery device could include a device such as a monitor/transmitter with ability to detect blood glucose levels, sense hormonal levels, and/or detect body temperature. The drug delivery device could include a device such as a monitor/transmitter an ability to communicate to the sensors/detectors in smartphone, an ability to transmit data to iCloud, and/or an ability to sense appetite sensing hormones.

In one embodiment, the drug delivery device could comprise a shell comprising a first material and a second material, wherein the second material comprises a biodegradable material; a core comprising a pharmaceutically effective composition, the core being enclosed by the shell; wherein the first material is distributed in a matrix of the biodegradable material; wherein the first material is configured to create holes in the shell; wherein the holes allow the pharmaceutically effective composition to be released to the exterior of the shell through the holes. In one embodiment, the shell could be made by polymerizing a silica-functionalized monomer to form a silica-containing biodegradable polymer shell.

In the drug delivery device, the pharmaceutically effective composition could comprise a targeting material or molecule that binds to a certain organ, object or a specific site within a body of a human or an animal. Thus, for example, even if the drug is the same but used for different cancers, then using a targeting molecule for a particular type of cancer, e.g., breast cancer, then the drug would bind to the cells of that particular type of cancer. On the other hand, if the drug is intended for ovarian cancer, then the target molecule could be specifically one that binds to the cells of ovarian cancer. The targeting material or molecule could be a biomarker.

An ingredient of the pharmaceutically effective composition could be a material that prevents the pharmaceutically effective composition from being taken up by the host defense as white blood and macrophages in the human or animal body. Such an ingredient remains in the blood but the body organs cannot take it up. An example of such an ingredient is polyethylene glycol (PEG), e.g., having 200 Dalton molecular weight.

In another embodiment, the biodegradable shell could contain a controlled release ingredient that functions as a control release sensor to control the release of the drug. For example, one would want a particular concentration of the drug at a given site over a given extended period of time. The control release ingredient could be a material that degrades faster than the remaining material of the biodegradable shell or punches holes (pores) in biodegradable shell.

The holes in the biodegradable shell could be punched by giving external stimuli such as sound, such as ultrasonic sound, radiation or microwave to the drug containing beads. The external stimulus heats up the controlled release ingredient, thereby punching one or more holes in the shell surrounding the controlled release ingredient, which could be a metal-containing material is configured to form holes in the shell, before or after implanting or attaching the device in or on a body of a human or an animal, when the shell is exposed to an external stimulus. For example, the controlled release ingredient that can be used for punching holes in the shell could be molecular iron such a magnetic resonance imaging (MRI) contrast agent. Depending on the concentration of the controlled release ingredient, one can control the number of holes punched in the shell, which in turn controls the amount of drug released from the core to the outside of the shell.

Two types of iron oxide MRI contrast agents exist: superparamagnetic iron oxide (SPIO) and ultrasmall superparamagnetic iron oxide (USPIO). These contrast agents consist of suspended colloids of iron oxide nanoparticles. A FDA approved iron oxide MRI contrast is Lumirem (also known as Gastromark).

Other controlled release ingredients for punching holes in the shell could be superparamagnetic iron platinum particles (SIPPs). SIPPs could also encapsulated with phospholipids to create multifunctional SIPP stealth immunomicelles that specifically targeted human prostate cancer cells.

Yet, other controlled release ingredients for punching holes in the shell are Mn-based nanoparticles. Manganese ions (Mn2+) are often used as a contrast agent in animal studies, usually referred to as MEMRI (Manganese Enhanced MRI). For example, Mn2+ carbon nanostructure complexes of graphene oxide nanoplatelets and graphene oxide nanoribbons could also be used as controlled release ingredients.

Uses Thereof:

Use of such device for systemic delivery any active pharmaceutical ingredient in humans or animals, as a patient convenience to avoid daily, weekly or monthly oral, subcutaneous or intravenous administration.

Use of such device for systemic delivery any biologic therapy in humans or animals as a means of patient convenience to overcome daily, weekly or monthly oral, subcutaneous or monthly administration. Biologic molecules can be peptides, antibodies or fragments thereof, nucleic acid molecules such as modified RNA, small interfering RNA, anti-sense DNA molecules or fragments thereof.

Use of such device to deliver antigens to elicit vaccine responses in humans or animals.

Use of such device to provide local tissue delivery of any therapeutic molecule, be it small molecule or biologic.

Use of such device to provide long-term sustained release of insulin or analogs thereof, alone or in combination of other therapies, to treat diabetes or other metabolic conditions.

Use of such device to provide long-term sustained release of GLP-1 or analogs thereof, alone or in combination of other therapies, to treat diabetes or other metabolic conditions.

Deposition of such device underneath the skin, or in fat tissue or in any specific organ for the purpose of long-term release of any therapeutic molecule, be it either a small molecule or biologic.

Specific use of such device to provide sustained long-term release of contraceptive hormones, combination of estrogen or progestin or singular delivery of progesterone alone and serve as contraceptive aid for women.

Specific use of such device for the intraocular delivery of any small molecule or biologic therapy as a means to provide the long-term therapeutic benefit for ocular diseases, such as age related macular degeneration, dry eye and various others.

Deposition of such device and use to directly into bladder for long-term delivery of any small molecule or biologic therapy to treat urinary bladder complications such as incontinence, yeast infections, bladder cancer and various others.

Deposition of such device and use to locally deliver therapeutic molecules to the male reproductive organs as a means to treat medical conditions such as erectile dysfunction, premature ejaculation, testicular cancer and various others pertaining to male reproductive system.

Deposition of such device and use to locally deliver therapeutic molecules to female reproductive organs, uterus and ovaries, to treat medical conditions such as endometriosis, uterine fibroids, ovarian cancer, uterine cancer, poly cystic ovarian syndrome, and various other disease pertaining to female reproductive system.

Deposition of such device and use to locally deliver therapeutic molecules to heart to treat conditions such as heart failure, myocardial ischemia, and various other heart diseases.

Deposition of such device and use to locally deliver therapeutic molecules into the adipose tissue to treat conditions such as metabolic syndrome, diabetes, hypercholesterolemia, hypertriglyceridemia and various others.

The advantages of the present invention will become readily apparent by those skilled in the art from the following detailed description, wherein it is shown and described preferred embodiments of the invention, simply by way of illustration of the best mode contemplated of carrying out the invention. As will be realized the invention is capable of other and different embodiments, and its several details are capable of modifications in various obvious respects, without departing from the invention. Accordingly, the description is to be regarded as illustrative in nature and not as restrictive.

INCORPORATION BY REFERENCE

All patents, application and publications referred to in this application are incorporated herein by reference in their entirety.

The invention claimed is:

1. A drug delivery product comprising sustained release particles, each sustained release particle comprising a shell and a core, wherein the shell comprises a first material and a second material, the second material comprising a first biodegradable material, wherein the core is enclosed by the shell and the core comprises a drug, wherein the first material is distributed in a matrix of the first biodegradable material, wherein the first material is configured to create holes in the shell and is selected from metallic particles, and wherein the holes allow the drug to be released to the exterior of the shell through the holes, the drug delivery product further comprising: an inner region, wherein the sustained release particles are enclosed in the inner region, and a skin or barrier layer at least partially surrounding the inner region; wherein the drug delivery product is substantially biodegradable when the drug delivery product is implanted within a body of a human or an animal such that the drug delivery product does not have to be removed from the body and is substantially biodegraded in the body, and wherein the skin or barrier layer controls the flow of the drug from the drug delivery product to a region outside of the drug delivery product such that the drug delivery product when implanted within the body provides a controlled delivery of the drug into the body.

2. The drug delivery product of claim 1, further comprises a second biodegradable material that biodegrades faster than the first biodegradable material over time.

3. The drug delivery product of claim 1, wherein the metallic particles comprise iron-containing or manganese-containing particles, or an iron-containing or manganese-containing polymer.

4. The drug delivery product of claim 1, wherein the drug comprises a targeting material or targeting molecule that binds to a certain organ, object or a specific site within a body of a human or an animal.

5. The drug delivery product of claim 1, wherein the first and second materials comprise polymers.

6. The drug delivery product of claim 1, wherein the first material comprises poly lactic acid (PLA) or an iron-containing polymer and the second material comprises poly ε-caprolactone (PCL).

7. The drug delivery product of claim 1, wherein the core comprises an emulsion of the drug and a polymer.

8. The drug delivery product of claim 1, wherein the core comprises drug containing beads.

9. The drug delivery product of claim 1, wherein the sustained release particles comprise beads, each bead comprising the shell and the core.

10. The drug delivery product of claim 1, wherein the drug delivery product is an implantable drug delivery device.

11. The drug delivery product of claim 1, wherein the sustained release particles are embedded in a biodegradable polymer matrix or a biodegradable foam.

12. The drug delivery product of claim 11, wherein the biodegradable polymer matrix or the biodegradable foam comprises a biodegradable sol-gel or a biodegradable thermoplastic polymer.

13. The drug delivery product of claim 11, wherein the skin or barrier layer comprises a third biodegradable material.

14. The drug delivery product of claim 13, wherein the first, second and third biodegradable materials have different compositions.

15. The drug delivery product of claim 13, wherein a time for biodegradability of the sustained release particles is shorter than a time for biodegradability of the biodegradable polymer matrix or the biodegradable foam in which the sustained release particles are embedded, and the time for biodegradability of the biodegradable polymer matrix or the biodegradable foam is shorter than a time for biodegradability of the skin or barrier layer surrounding the biodegradable polymer matrix or the biodegradable foam.

16. The drug delivery product of claim 1, wherein the metallic particles are configured to form holes in the shell, before or after implanting or attaching the drug delivery product in or on a body of a human or an animal, when the shell is exposed to an external stimulus.

17. The drug delivery product of claim 1, wherein the metallic particles comprise an iron-containing polymer.

18. The drug delivery product of claim 1, wherein the metallic particles comprise molecular iron or iron platinum particles.

19. The drug delivery product of claim 18, wherein the molecular iron comprises iron oxide.

* * * * *